(12) United States Patent
Katsura et al.

(10) Patent No.: US 7,793,546 B2
(45) Date of Patent: Sep. 14, 2010

(54) ULTRASONIC FLAW DETECTION METHOD AND ULTRASONIC FLAW DETECTION DEVICE

(75) Inventors: Hiroaki Katsura, Osaka (JP); Yoichiro Ueda, Osaka (JP); Kazuya Ushirokawa, Osaka (JP)

(73) Assignee: Panasonic Corporation, Osaka (JP)

( * ) Notice: Subject to any disclaimer, the term of this patent is extended or adjusted under 35 U.S.C. 154(b) by 383 days.

(21) Appl. No.: 11/918,327

(22) PCT Filed: Jun. 12, 2006

(86) PCT No.: PCT/JP2005/311737

§ 371 (c)(1),
(2), (4) Date: Oct. 12, 2007

(87) PCT Pub. No.: WO2007/007500

PCT Pub. Date: Jan. 18, 2007

(65) Prior Publication Data

US 2009/0301201 A1 Dec. 10, 2009

(30) Foreign Application Priority Data

Jul. 11, 2005 (JP) ............................. 2005-201016

(51) Int. Cl.
*G01N 29/28* (2006.01)
(52) U.S. Cl. ..................................... 73/644
(58) Field of Classification Search ................... 73/644, 73/617, 629
See application file for complete search history.

(56) References Cited

U.S. PATENT DOCUMENTS

| | | | | |
|---|---|---|---|---|
| 3,964,296 A | * | 6/1976 | Matzuk | 73/607 |
| 4,130,112 A | * | 12/1978 | Frazer | 600/448 |
| 6,485,420 B1 | * | 11/2002 | Bullis | 600/437 |
| 2002/0189359 A1 | * | 12/2002 | Batzinger et al. | 73/596 |
| 2008/0053230 A1 | * | 3/2008 | Katsura et al. | 73/571 |

FOREIGN PATENT DOCUMENTS

| | | |
|---|---|---|
| JP | 2003-177117 | 6/2003 |
| JP | 2003-185640 | 7/2003 |
| JP | 2003-254953 | 9/2003 |
| JP | 2004-077342 | 3/2004 |
| JP | 2004-239654 | 8/2004 |

* cited by examiner

*Primary Examiner*—Hezron Williams
*Assistant Examiner*—Rose M Miller
(74) *Attorney, Agent, or Firm*—Steptoe & Johnson LLP

(57) ABSTRACT

An ultrasonic transmission medium is received in a medium container, and an opening of the container is sealed by a polymer membrane. An inspection object is received in an inspection object receiving container body that is separate from the medium container and whose opening is formed opposite the polymer membrane of the medium container. The opening of the inspection object receiving container body is covered by the polymer membrane of the medium container, and a measurement environment space formed by a frame body, the polymer membrane, and the inspection object is reduced in pressure to cause the polymer membrane to be in intimate contact with the inspection object. Then, flaw detection is performed by emitting and applying an ultrasonic wave from an ultrasonic probe to the inspection object via the ultrasonic transmission medium and the polymer membrane.

3 Claims, 7 Drawing Sheets

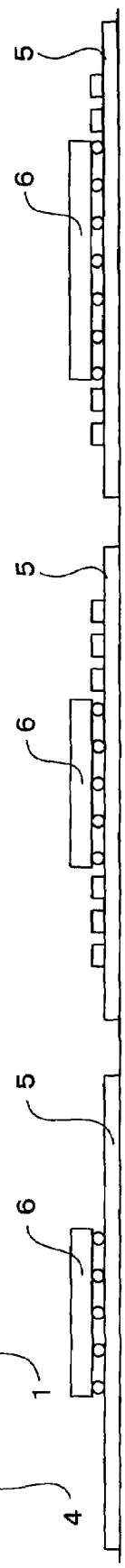
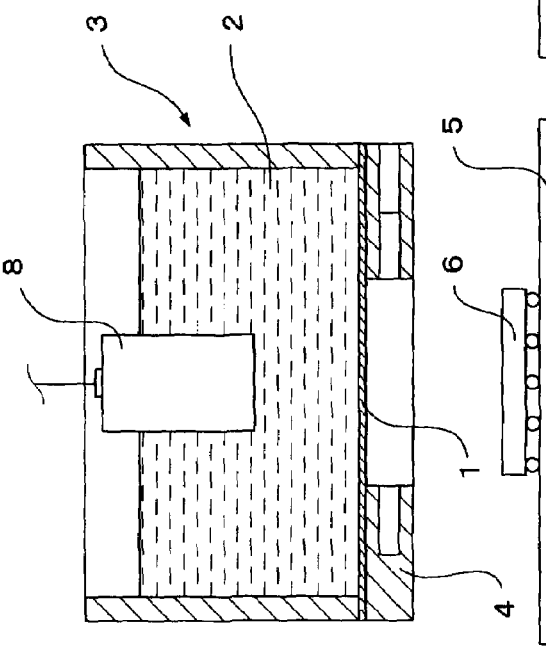
FIG. 5A PRIOR ART
FIG. 5B PRIOR ART
FIG. 5C PRIOR ART

ULTRASONIC FLAW DETECTION METHOD AND ULTRASONIC FLAW DETECTION DEVICE

TECHNICAL FIELD

The present invention relates to an ultrasonic flaw detection method of inspecting an inspection object such as an electronic element in a dry process.

BACKGROUND ART

In recent years, as one means for accomplishing a decrease in size and thickness of products, electronic elements such as BGA or CSP have been spread which have a rear-face electrode so as to reduce a mounting area. Since it is difficult to inspect connection portions by the use of optical means at the time of using rear-face electrode elements, another means for assuring qualities is required.

In the past, examples of a method of inspecting the insides of electronic elements have included a radiographic inspection method and an ultrasonic flaw detection method. The radiographic inspection method is very effective for checking a disconnection, short circuit and volume anomaly, but it is not suitable to check the separation or the like of the connection portion. Since ultrasonic waves are reflected from portions varying in acoustic property, the ultrasonic flaw detection method is suitable to check the separation or the like of the connection portion, but the inspection object is immersed in a liquid as an ultrasonic transmission medium and an ultrasonic wave is emitted to and received from the inspection object via the liquid to perform the flaw detection. However, the inspection object is immersed in the liquid and thus an electrode material of the inspection object is eluted to the liquid in an ionic form, whereby the reliability deteriorates and according to the property of immersing the inspection object in the liquid, whereby the ultrasonic flaw detection cannot be performed in a production field.

Japanese Unexamined Patent Application Publication No. 2003-177117 discloses a dry ultrasonic flaw detection method of inspecting an inspection object without immersing the inspection object in a liquid. As shown in FIG. 5, a container 3 is used which has only a bottom surface sealed by a polymer membrane 1 and receives an ultrasonic transmission medium 2 therein. As shown in FIG. 6A, an inspection object element 6 is received inside a connection body 4 by pressing the frame-shaped connection body 4 provided at the bottom of the container 3 on an inspection object substrate 5 and a space between the inspection object substrate 5 and the polymer membrane 1 is depressurized by connecting the inside of the connection body 4 to a depressurization device 7a, thereby bringing the polymer membrane 1 into close contact with the inspection object element 6. Accordingly, an ultrasonic wave is emitted from an ultrasonic probe 8 to the inspection object element 6 via the ultrasonic transmission medium 2 and the polymer membrane 1, and a reflection wave is received at the ultrasonic probe 8 to perform flaw detection.

DISCLOSURE OF THE INVENTION

Problem to be Solved by the Invention

However, in the dry ultrasonic flaw detection method disclosed in Japanese Unexamined Patent Application Publication No. 2003-177117, even by allowing a depressurization device 7a to depressurize a space between the inspection object substrate 5 and the polymer membrane 1, it is not possible to bring the polymer membrane 1 into close contact with the inspection object element 6, whereby it is not possible to perform flaw detection on the inspection object substrate 5 having high mounting efficiency, in which other electronic elements 9 are mounted adjacent to the inspection object element 6 as shown in FIG. 6B.

When an inspection object area of the inspection object element 6 is great as shown in FIG. 6C and thus it is not possible to bring the polymer membrane 1 into close contact with only a part of the inspection object element 6, it is not possible to perform the flaw detection for areas A and B.

An object of the invention is to provide an ultrasonic flaw detection device capable of inspecting the inspection object substrate 5 having high mounting efficiency or the great inspection object area.

Means for Solving the Problem

According to a first aspect of the invention, an ultrasonic flaw detection method includes, when an ultrasonic transmission medium comes in contact with an inspection object with a polymer membrane interposed therebetween and an ultrasonic probe ultrasonically inspects the inspection object via the ultrasonic transmission medium, receiving the inspection object in an inspection object receiving container body of which an opening is formed opposite the polymer membrane of a medium container, independently of the medium container, which receives the ultrasonic transmission medium and has an opening sealed by the polymer membrane; covering the opening of the inspection object receiving container body with the polymer membrane of the medium container by relatively moving the medium container and the inspection object receiving container body; bringing the polymer membrane into close contact with the inspection object by depressurizing a measurement environment space formed by a frame body incorporated into or connected to the inspection object receiving container body, the polymer membrane, and the inspection object; and emitting an ultrasonic wave from the ultrasonic probe to the inspection object via the ultrasonic transmission medium and the polymer membrane to perform flaw detection.

According to a second aspect of the invention, an ultrasonic flaw detection device for bringing an ultrasonic transmission medium into close contact with an inspection object with a polymer membrane interposed therebetween and allowing an ultrasonic probe to ultrasonically inspect the inspection object via the ultrasonic transmission medium includes a medium container which receives the ultrasonic transmission medium and has an opening sealed by a polymer membrane; an inspection object receiving container body which is provided independently of the medium container and which receives the inspection object and has an opening formed opposite the polymer membrane of the medium container; a frame body which is incorporated into or connected to the inspection object receiving container body and which forms a measurement environment space with the polymer membrane and the inspection object; depressurization means for bringing the polymer membrane into close contact with the inspection object by depressurizing the measurement environment space formed by the polymer membrane, the inspection object, and the frame body; and an ultrasonic probe which emits an ultrasonic wave to the inspection object via the ultrasonic transmission medium and the polymer membrane. With this configuration, a support contacting and supporting a face opposite to an inspection object face of an electronic circuit substrate as the inspection object is formed in the inspection object receiving container body. An inside of the inspection object receiving container body is partitioned into a pressurization chamber and a receiving chamber of the electronic circuit substrate as an inspection object with a flexible diaphragm.

According to a third aspect of the invention, an ultrasonic flaw detection method includes, when an ultrasonic transmission medium comes in contact with an inspection object with a polymer membrane interposed therebetween and an ultrasonic probe ultrasonically inspects the inspection object via the ultrasonic transmission medium, receiving the inspection object in a receiving chamber of an inspection object receiving container body which has an opening formed opposite a polymer membrane of a medium container, has an inside partitioned into a pressurization chamber and the receiving chamber of an electronic circuit substrate as the inspection object with a flexible diaphragm, independently of the medium container which receives the ultrasonic transmission medium and has an opening sealed by the polymer membrane; covering the opening of the inspection object receiving container body with the polymer membrane of the medium container by relatively moving the medium container and the inspection object receiving container body; bringing the polymer membrane into close contact with the inspection object by depressurizing the measurement environment space formed by the polymer membrane, the inspection object, and a frame body incorporated into or connected to the inspection object receiving container body; supporting the inspection object by the use of the diaphragm by pressurizing the pressurization chamber of the inspection object receiving container body; and emitting an ultrasonic wave from the ultrasonic probe to the inspection object via the ultrasonic transmission medium and the polymer membrane to perform flaw detection.

In any one of the above-mentioned ultrasonic flaw detection methods, a front surface of the polymer membrane is smeared with alcohol before or after injecting the ultrasonic transmission medium into the medium container at the time of covering the opening of the inspection object receiving container body with the polymer membrane of the medium container by relatively moving the medium container and the inspection object receiving container body.

Effects Of The Invention

According to an ultrasonic flaw detection method and an ultrasonic flaw detection device of the invention, it is possible to implement ultrasonic flaw detection suitable for a production field for inspecting an inspection object such as an electronic element on a mounting substrate, which requires a precise inspection, in a dry process.

BRIEF DESCRIPTION OF THE DRAWINGS

FIG. 5 is a cross-sectional view of a known ultrasonic flaw detection device and a side view of an inspection object substrate mounted with an inspection object element.

BEST MODE FOR CARRYING OUT THE INVENTION

Hereinafter, an ultrasonic flaw detection method according to embodiments of the invention will be described with reference to FIGS. 1 to 4 and FIG. 7.

First Embodiment

Figure 1A:
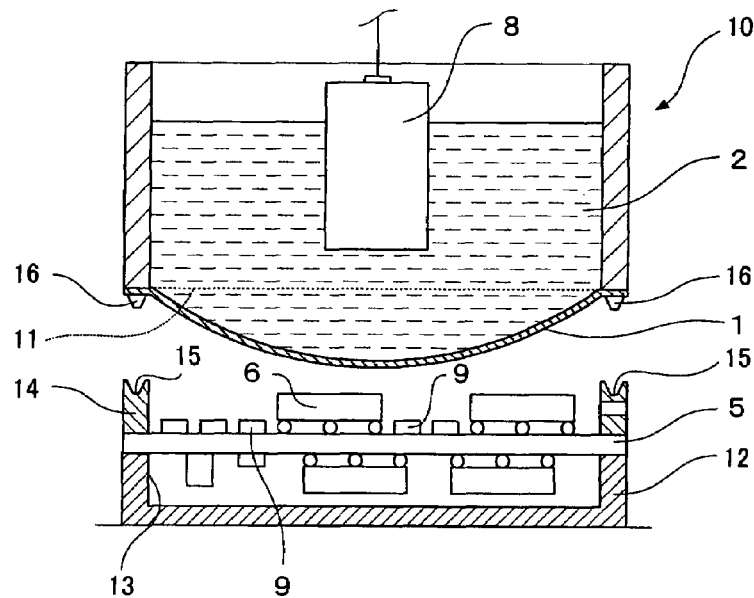
FIG. 1 is a diagram showing an inspection process in an ultrasonic flaw detection method according to a first embodiment of the invention.
Figure 1B:
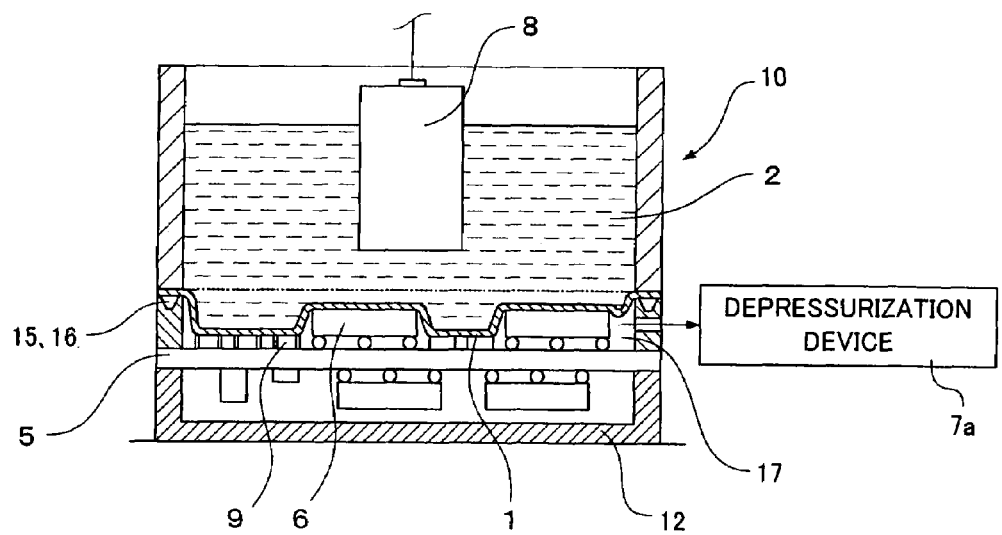

FIGS. 1A and 1B show a first embodiment of the invention.

An opening 11 at the bottom of a medium container 10 is sealed by a polymer membrane 1 and an ultrasonic transmission medium 2 is received inside the medium container 10. Reference numeral 8 denotes an ultrasonic probe.

An inspection object receiving container body 12, whose opening 13 is formed opposite the polymer membrane 1, is a box body having a bottom, provided independently of the medium container 10. In FIG. 1A, an inspection object substrate 5 mounted with an inspection object element 6 is received in the inspection object receiving container body 12 with a mounting surface of the inspection object element 6 facing upward. The inspection object substrate 5 is interposed between a frame body 14 and the inspection object receiving container body 12.

Convex portions 16 corresponding to concave portions 15 formed on an end face of the frame body 14 are formed at the bottom of the medium container 10.

As shown in FIG. 1A, the inspection object substrate 5 and the frame body 14 are set in the inspection object receiving container body 12, and then the medium container 10 is disposed in the inspection object receiving container body 12 so that the convex portions 16 of the medium container 10 engage with the concave portions 15 of the frame body 14. A measurement environment space 17 formed by the frame body 14, the polymer membrane 1 and the inspection object substrate 5 is depressurized by operating a depressurization device 7a.

As shown in FIG. 1B, the polymer membrane 1 is brought into close contact with the inspection object element 6 by the depressurization. Next, a distance between the ultrasonic probe 8 and the inspection object element 6 is adjusted and set so that an ultrasonic wave emitted from the ultrasonic probe 8 is reflected from a position of the inspection object element 6 corresponding to a desired depth and the reflected ultrasonic wave is received at the ultrasonic probe 8, the ultrasonic wave is emitted, the ultrasonic wave reflected from the inspection object element 6 is received at the ultrasonic probe 8, and a solidity of a desired position of an inspection portion is inspected from a difference between a transmission time and a reception time.

As described above, the entirety of the inspection object substrate 5 is depressurized with being received in the inspection object receiving container body 12 to bring the polymer membrane 1 into close contact with the inspection object element 6 by an operation of the frame body 14 even though another electronic element 9 is mounted adjacent to the inspection object element 6 of the inspection object substrate 5, whereby it is possible to perform an accurate ultrasonic flaw detection. It is possible to perform the ultrasonic flaw detection even though the inspection object range is broader than that in the related art.

Since the inspection object substrate 5 is set in the inspection object receiving container body 12 provided independently of the medium container 10 and measured, it is possible to hold the inspection object substrate 5 parallel, whereby it is possible to start the measurement in a short time.

Even though the medium container 10 is adapted to be attachable and detachable to the frame body 14 in which the inspection object substrate 5 is set and the inspection object receiving container body 12, the concave portions 15 and the convex portions 16 engaging with each other are formed, and thus an alignment between them is accurate.

Even when a through-hole communicated with the inspection object substrate 5 exists or an element inserting hole in which an element is not mounted remains, the inspection object receiving container body 12 covers and closes a rear face of the inspection object substrate 5. Therefore, since the depressurization device 7a depressurizes an inside of the inspection object receiving container body 12 and the measurement environment space 17 via the element inserting hole, it is possible to solve a defective close contact of the polymer membrane 1 with the inspection object element 6.

Second Embodiment

Figure 2A:
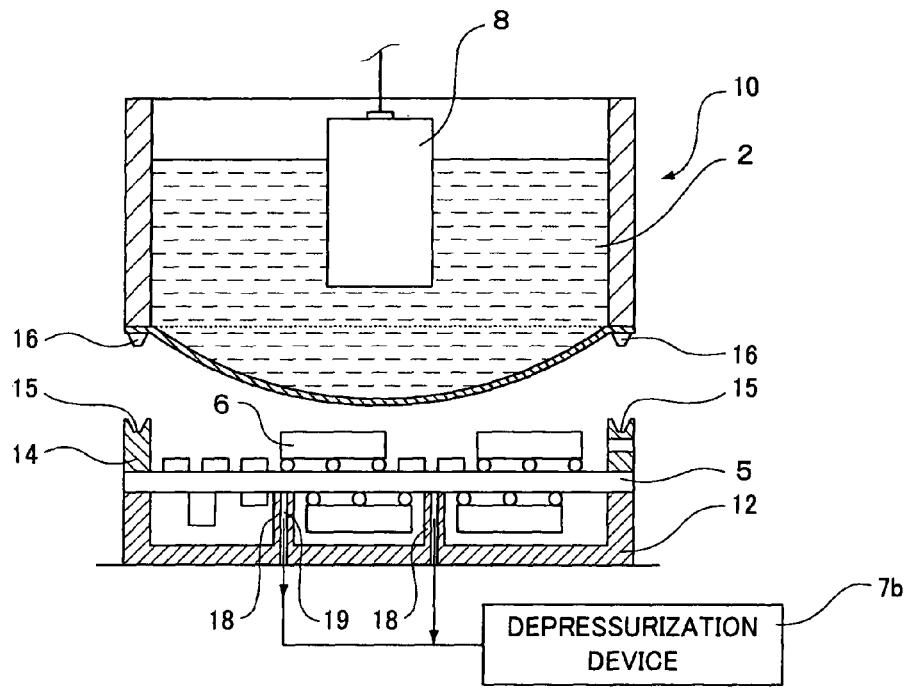
FIG. 2 is a diagram showing an inspection process in an ultrasonic flaw detection method according to a second embodiment of the invention.
Figure 2B:
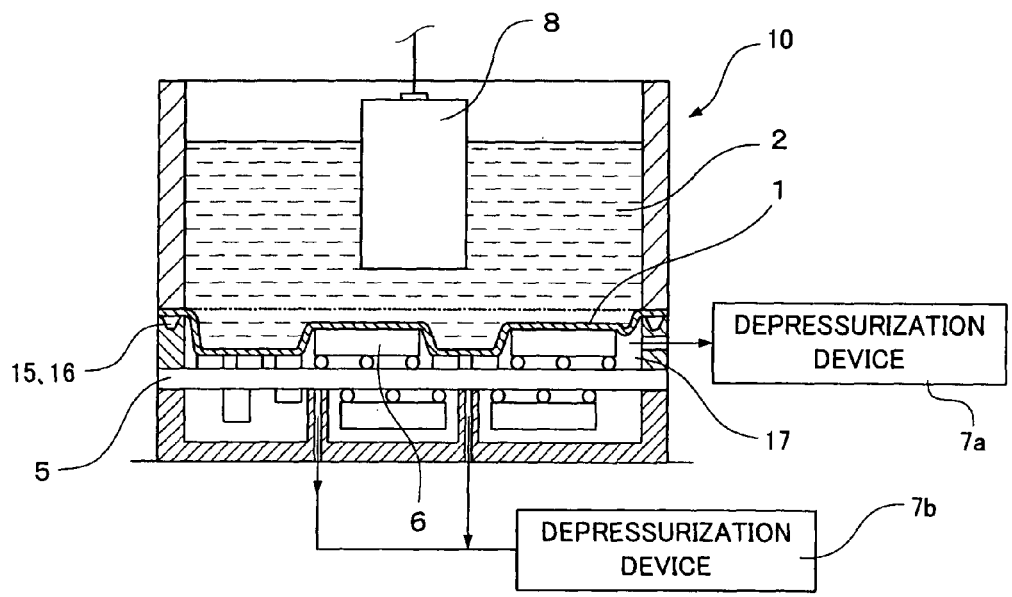

FIGS. 2A and 2B show a second embodiment of the invention.

In the first embodiment described above, the inspection object substrate 5 is interposed between the inspection object receiving container body 12 and the frame body 14 in an outer peripheral portion thereof, but in the second embodiment, supporters 18 abutting on the rear face of the inspection object substrate 5 are formed in the inspection object receiving container body 12. Aspiration holes open at ends of the supporters 18. Others are the same as the first embodiment.

With this configuration, when the inspection object substrate 5 is set, aspiration holes 19 of the supporters 18 are depressurized by a depressurization device 7b to adsorb and retain the set inspection object substrate 5. Then, as shown in FIG. 2B, the medium container 10 is placed so that the convex portions 16 of the medium container 10 engage with the concave portions 15 of the frame body 14. The measurement environment space 17, which is formed by the frame body 14, the polymer membrane 1 and the inspection object substrate 5, is depressurized by operating the depressurization device 7a to perform the ultrasonic flaw detection.

As described above, the supporter 18 supports the inspection object substrate 5, and thus, a planarity of the inspection object substrate 5 is improved further than that of the first embodiment, whereby it is possible to expect a more accurate flaw detection.

Third Embodiment

Figure 3A:
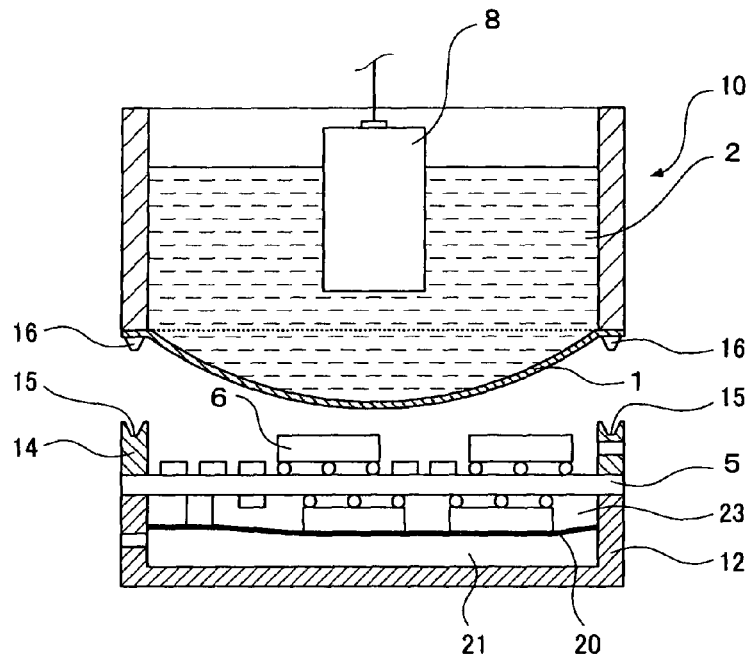
FIG. 3 is a diagram showing an inspection process in an ultrasonic flaw detection method according to a third embodiment of the invention.
Figure 3B:
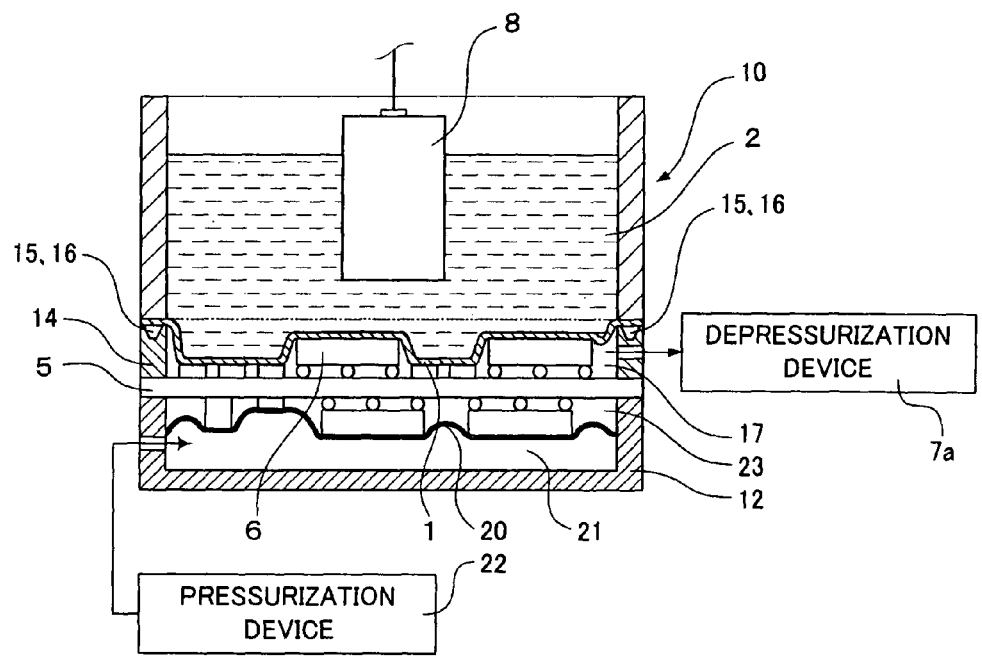

FIGS. 3A and 3B show a third embodiment of the invention.

In the first embodiment described above, the inspection object substrate 5 is interposed between the inspection object receiving container body 12 and the frame body 14 in the outer peripheral portion thereof, but in the third embodiment, a flexible diaphragm 20 is formed in the inspection object receiving container body 12. A pressurization chamber 21 formed between the diaphragm 20 and a bottom of the inspection object receiving container body 12 is adapted to be pressurized by a pressurization device 22. Others are the same as the first embodiment.

With this configuration, when the inspection object substrate 5 is set, the inspection object substrate 5 is set in a receiving chamber 23 inside the inspection object receiving container body 12 of which inside is partitioned into the pressurization chamber 21 and the receiving chamber 23 by the diaphragm 20 as shown in FIG. 3A.

Next, as shown in FIG. 3B, the medium container 10 is placed so that the convex portions 16 of the medium container 10 engage with the concave portions 15 of the frame body 14. The measurement environment space 17 formed by the frame body 14, the polymer membrane 1 and the inspection object substrate 5 is depressurized by operating the depressurization device 7 and the pressurization chamber 21 is pressurized by operating the pressurization device 22, and thus a rear face of the inspection object substrate 5 is pressed by the diaphragm 20 to support the inspection object substrate 5. Accordingly, the planarity of the inspection object substrate 5 is improved further than that of the first embodiment, whereby it is possible to expect the more accurate flaw detection.

Fourth Embodiment

Figure 4A:
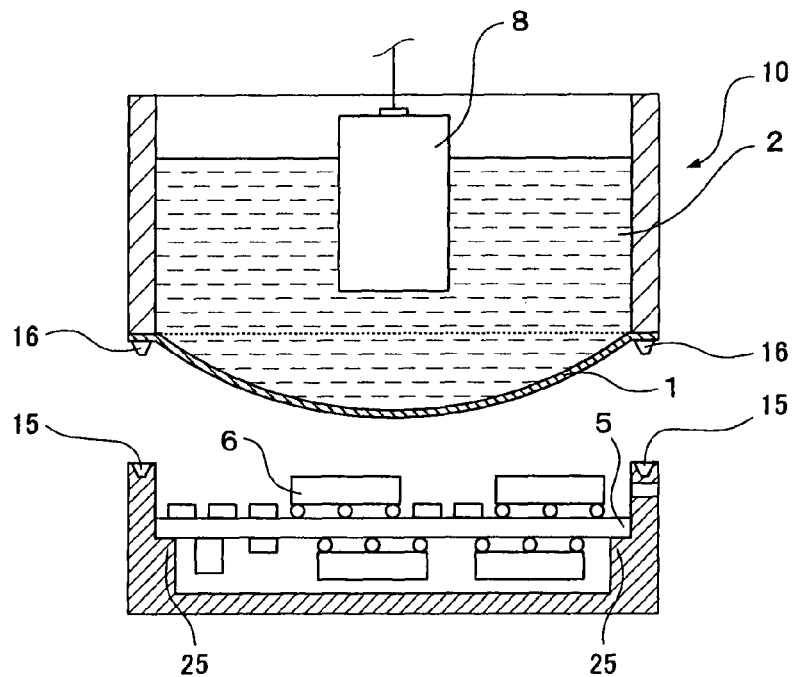
FIG. 4 is a diagram showing an inspection process in an ultrasonic flaw detection method according to a fourth embodiment of the invention.
Figure 4B:
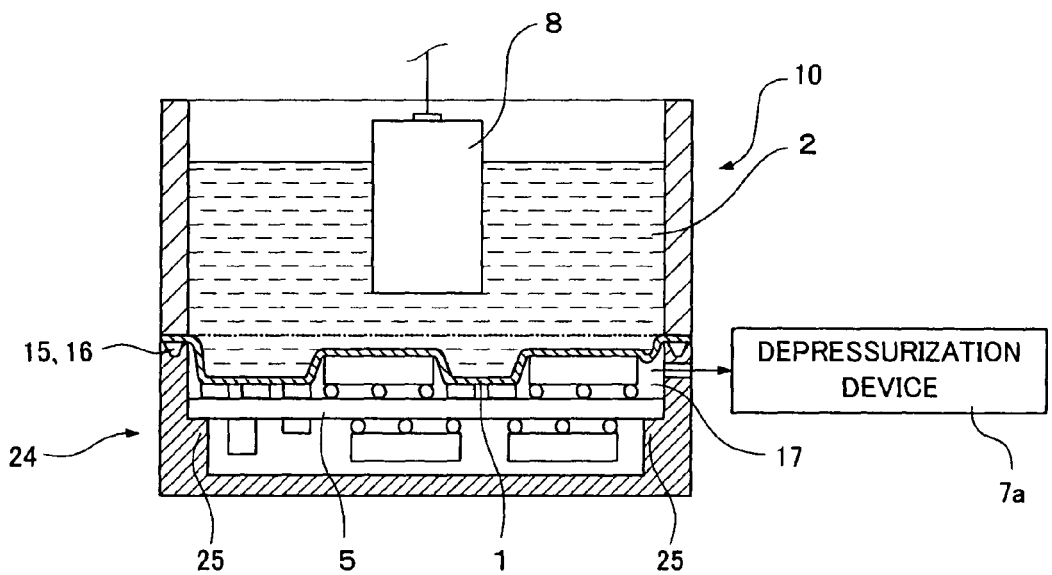
Figure 6A:
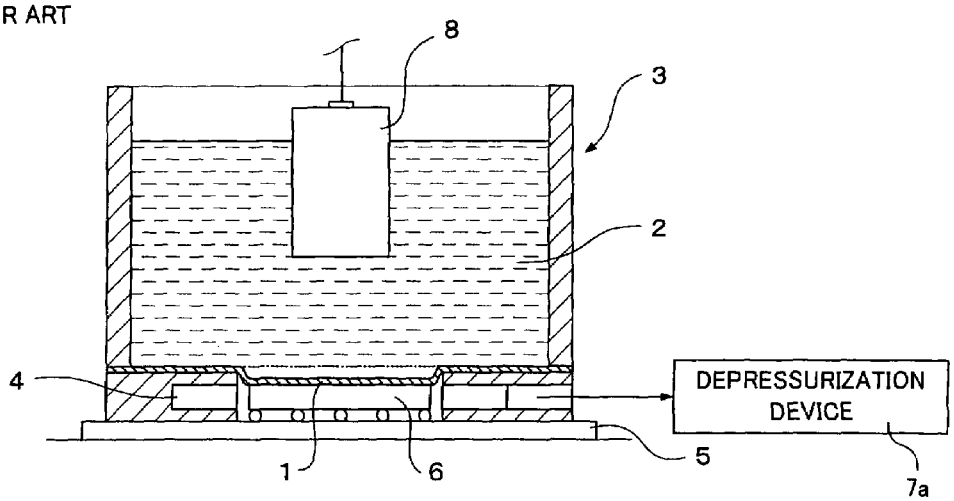
FIG. 6 is a cross-sectional view in a known ultrasonic flaw detection method under measurement.
Figure 6B:
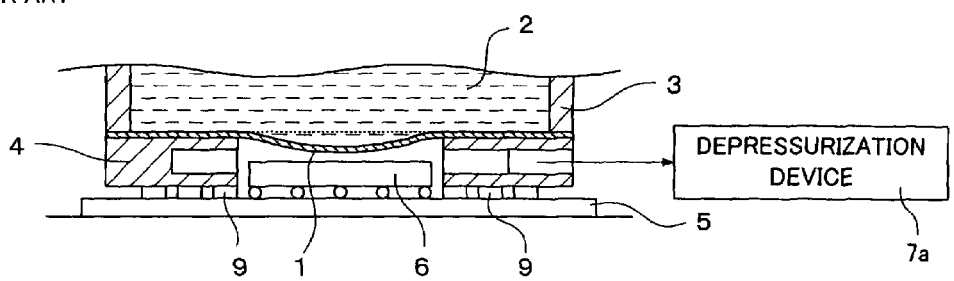
Figure 6C:
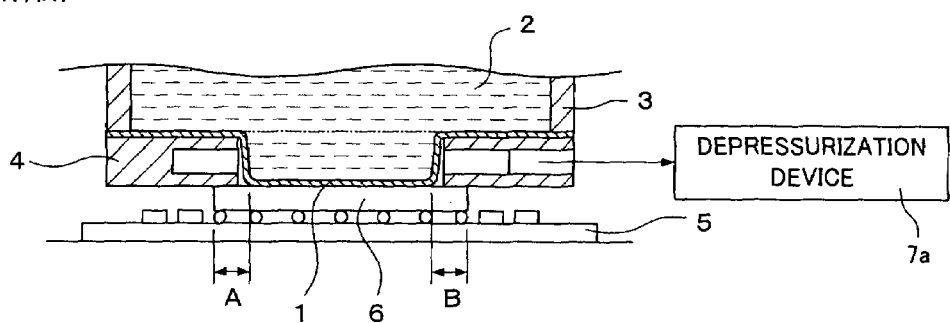

FIGS. 4A and 4B show a fourth embodiment of the invention.

In the embodiments described above, the inspection object receiving container body 12 is independent from the frame body 14, but an inspection object receiving container 24 may be integrally constituted by the both bodies as shown in FIG. 4. Specifically, shoulders 25 are formed at inner peripheries of the inspection object receiving container 24 and the inspection object substrate 5 is placed in the shoulders 25, and thus the inspection object substrate 5 is set at an intermediate portion of the inspection object receiving container 24 in a depth direction as shown in FIG. 4A. Then, the medium container 10 is disposed so that the convex portions 16 of the medium container 10 engage with the concave portions 15 of the inspection object receiving container 24 as shown in FIG. 4B. The measurement environment space 17 is depressurized by operating the depressurization device 7a to perform the ultrasonic flaw detection.

Fifth Embodiment

Figure 7B:
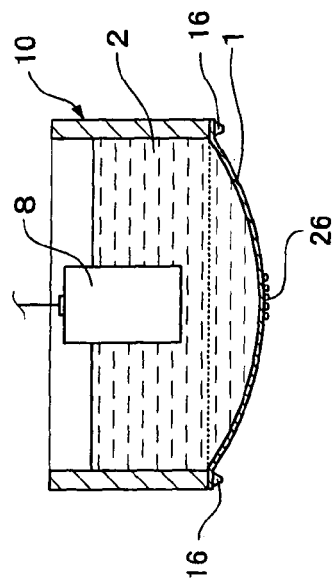
FIG. 7 is a process diagram of a principal part in an ultrasonic flaw detection method according to a fifth embodiment of the invention.
Figure 7D:
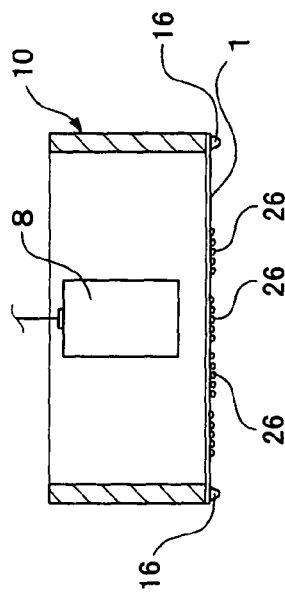
Figure 7A:
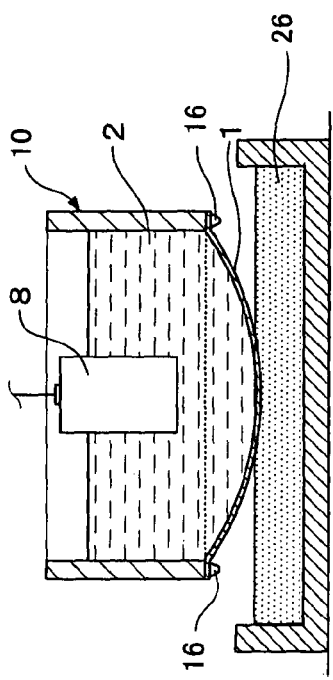

In the ultrasonic flaw detection method according to the embodiments of the invention, the polymer membrane 1 abuts on the inspection object element 6 as it is, but the polymer membrane 1 set in the medium container 10 is immersed in alcohol 26 as shown in FIG. 7A, a front face of the polymer membrane 1 is wetted with the alcohol 26 as shown in FIG. 7B, and then the inspection object element 6 is pressed with the polymer membrane 1, whereby it is possible to prevent a decrease in inspection accuracy resulting from the concavity and convexity of the front face of the inspection object element 6.

Specifically, when the polymer membrane 1 is put in the alcohol 26, the ultrasonic transmission medium 2 is already injected into the medium container 10, and a center of the polymer membrane 1 is swelled downwardly. When the medium container 10 is pulled up, alcohol 33 smeared on the polymer membrane 1 concentrates in the center of the polymer membrane 1.

In this state, the polymer membrane 1 comes in contact with the front face of the inspection object element 6, and thus the alcohol 26 concentrating in the center of the polymer membrane 1 first comes in contact with an upper center of the inspection object element 6 and the concavity and convexity (not shown) in the upper center of the inspection object element 6 is wetted with the alcohol 26. Accordingly, the alcohol 26 enters a concave portion in the upper center of the inspection object element 6. The medium container 10 comes closer to the inspection object element 6 and as the polymer membrane 1 comes in contact, outwardly from the upper center of the inspection object element 6, the excess alcohol 26 supplied to the upper center of the inspection object elopement 6 spreads outwardly from the inspection object element 6 of which concave portion is filled with the excess alcohol 26, and the inspection object element 6 comes into close contact with the polymer membrane 1 in a vacuum state. Since the excess alcohol 26 removed from a space between the inspection object element 6 and the polymer membrane 1 evaporates and is not left on the substrate 6, the excess alcohol 26 does not affect an electrical performance.

As described above, even though the concavity and convexity appears on the front face of the inspection object element 6, it is possible to bring the polymer membrane 1 into close contact with the inspection object element 6 by smearing the inspection object element 6 with the alcohol 26, whereby the inspection accuracy is improved further compared with the case where air remains in the concave portions on the front face of the inspection object element 6.

Isopropyl alcohol, ethanol and methanol can be used as the alcohol 26.

Figure 7C:
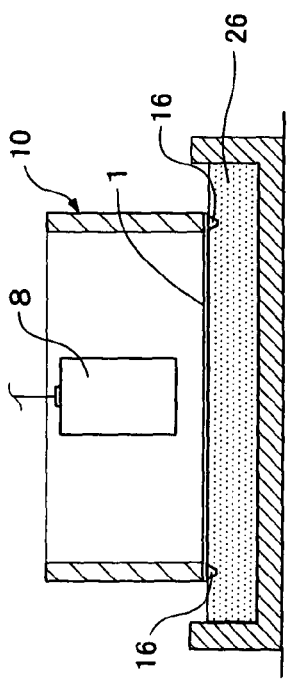

In FIGS. 7A and 7B, the polymer membrane 1 is immersed in the alcohol 26 with the ultrasonic transmission medium 2 already injected into the medium container 10, but even when the polymer membrane 1 is immersed in the alcohol 26 with the ultrasonic transmission medium 2 not yet injected into the medium container 26 as shown in FIG. 7C and the medium container 10 is pulled up as shown in FIG. 7D, and then the ultrasonic transmission medium 2 is injected into the medium container 10, it is possible to expect the same effect.

In the embodiments described above, after the inspection object substrate 5 and the frame body 14 are set in the inspection object receiving container body 12, the medium container 10 is placed so that the convex portions 16 of the medium container 10 engage with the concave portions 15 of the frame body 14, but the frame body 14 in which the inspection object substrate 5 is set and the inspection object receiving container body 12 approach or come close to the medium container 10, whereby the convex portions 16 of the medium container 10 may engage with the concave portions 15 of the frame body 14.

INDUSTRIAL APPLICABILITY

The invention can implement accurate ultrasonic flaw detection without wetting an inspection object in the production process and thus can be used for an in-line inspection of an electronic substrate mounted with various semiconductor devices.

The invention claimed is:

1. An ultrasonic flaw detection device for bringing an ultrasonic transmission medium into close contact with an inspection object with a polymer membrane interposed therebetween and for ultrasonically inspecting the inspection object via the ultrasonic transmission medium, the ultrasonic flaw detection device comprising:

a medium container for containing an ultrasonic transmission medium, and having an opening which is sealed by a polymer membrane;

an inspection object receiving container body for receiving an inspection object and having an opening where an inspection portion of a received inspection object is exposed;

a frame body incorporated into or connected to the inspection object receiving container body, and with the polymer membrane defining a measurement environment space for an inspection object;

a flexible diaphragm which partitions an inside of the inspection object receiving container body into a pressurization chamber and a receiving chamber of the electronic circuit substrate, for an inspection object;

a depressurization unit for bringing the polymer membrane into close contact with an inspection object by depressurizing the measurement environment space; and an ultrasonic probe for transmitting and receiving an ultrasonic wave to and from an inspection object via the ultrasonic transmission medium and the polymer membrane.

2. An ultrasonic flaw detection method wherein a polymer membrane containing an ultrasonic transmission medium comes in contact with an inspection object, and an ultrasonic probe ultrasonically inspects such an inspection object through the ultrasonic transmission medium, the method comprising:

receiving an inspection object in a receiving chamber of an inspection object receiving container body which has an inside partitioned by a flexible diaphragm into a pressurization chamber and the receiving chamber of an electronic circuit substrate as an inspection object and an inspection portion of the received inspection object is exposed through an opening in the receiving container body covering the opening with the polymer membrane by relatively moving the medium container and the inspection object receiving container body;

bringing the polymer membrane into close contact with the inspection object by depressurizing the measurement environment space formed by the polymer membrane, the inspection object, and a frame body incorporated into or connected to the inspection object receiving container body;

supporting the inspection object by flexible diaphragm by pressurizing the pressurization chamber of the inspection object receiving container body; and emitting an ultrasonic wave from the ultrasonic probe to the inspection object via the ultrasonic transmission medium and the polymer membrane to perform flaw detection.

3. The ultrasonic flaw detection method according to claim 2, wherein a front surface of the polymer membrane is smeared with alcohol before covering the opening with the polymer membrane by relatively moving the medium container and the inspection object receiving container body.

* * * * *

UNITED STATES PATENT AND TRADEMARK OFFICE
CERTIFICATE OF CORRECTION

| | | |
|---|---|---|
| PATENT NO. | : 7,793,546 B2 | Page 1 of 1 |
| APPLICATION NO. | : 11/918327 | |
| DATED | : September 14, 2010 | |
| INVENTOR(S) | : Hiroaki Katsura et al. | |

It is certified that error appears in the above-identified patent and that said Letters Patent is hereby corrected as shown below:

The title page is corrected as follows and should read:

(86) PCT No.: PCT/JP2006/311737

Signed and Sealed this

Twenty-first Day of December, 2010

David J. Kappos
*Director of the United States Patent and Trademark Office*